(12) United States Patent
Kadkhodayan et al.

(10) Patent No.: US 7,485,734 B2
(45) Date of Patent: Feb. 3, 2009

(54) SEAL SWELL AGENT AND PROCESS THEREFOR

(75) Inventors: Abbas Kadkhodayan, Collinsville, IL (US); Nubar Ozbalik, Midlothian, VA (US)

(73) Assignee: Afton Chemical Corporation, Richmond, VA (US)

( * ) Notice: Subject to any disclaimer, the term of this patent is extended or adjusted under 35 U.S.C. 154(b) by 602 days.

(21) Appl. No.: 11/046,073

(22) Filed: Jan. 28, 2005

(65) Prior Publication Data

US 2006/0173217 A1 Aug. 3, 2006

(51) Int. Cl.
C07D 333/48 (2006.01)
(52) U.S. Cl. .................... 549/67; 252/72; 252/78.1; 508/303; 568/32
(58) Field of Classification Search .............. 568/32; 252/72, 78.1; 549/78, 67; 508/303
See application file for complete search history.

(56) References Cited

U.S. PATENT DOCUMENTS

| | | | |
|---|---|---|---|
| 2,284,409 A | 5/1942 | Erath | |
| 2,284,410 A | 5/1942 | Farmer | |
| 2,305,619 A * | 12/1942 | Kelley et al. | ............... 554/199 |
| 2,393,925 A * | 1/1946 | Morris et al. | ............... 514/66 |
| 2,452,949 A | 11/1948 | Morris et al. | |
| 2,724,649 A * | 11/1955 | Julian et al. | ............... 426/604 |
| 2,749,311 A | 6/1956 | Sabol et al. | |
| 2,760,933 A | 8/1956 | Fields et al. | |
| 2,765,289 A | 10/1956 | Fields et al. | |
| 2,849,318 A * | 8/1958 | Julian et al. | ............... 554/3 |
| 2,850,453 A | 9/1958 | Fields | |
| 2,910,439 A | 10/1959 | Fields | |
| 3,172,892 A | 3/1965 | Suer et al. | |
| 3,254,025 A | 5/1966 | Le Suer | |
| 3,281,428 A | 10/1966 | Le Suer | |
| 3,282,955 A | 11/1966 | Le Suer | |
| 3,338,832 A | 8/1967 | Le Suer | |
| 3,344,069 A | 9/1967 | Stuebe | |
| 3,361,673 A | 1/1968 | Stuart et al. | |
| 3,407,140 A | 10/1968 | Chiddix et al. | |
| 3,533,945 A | 10/1970 | Vogel | |
| 3,658,839 A | 4/1972 | Vineyard | |
| 3,663,561 A | 5/1972 | Blaha | |
| 3,676,089 A | 7/1972 | Morris | |
| 3,703,536 A | 11/1972 | Piasek et al. | |
| 3,718,663 A | 2/1973 | Piasek et al. | |
| 3,840,549 A | 10/1974 | Blaha et al. | |
| 3,862,798 A | 1/1975 | Hopkins | |
| 4,029,587 A | 6/1977 | Koch | |
| 4,029,588 A * | 6/1977 | Koch | ............... 508/303 |
| 4,036,299 A * | 7/1977 | Cha et al. | ............... 166/261 |
| 4,116,877 A | 9/1978 | Outten et al. | |
| 4,234,435 A | 11/1980 | Meinhardt et al. | |
| 4,455,243 A | 6/1984 | Liston | |
| 4,496,691 A | 1/1985 | Proux et al. | |
| 4,652,387 A | 3/1987 | Andress, Jr. et al. | |
| 4,927,554 A | 5/1990 | Jolley et al. | |
| 4,943,672 A | 7/1990 | Hamner et al. | |
| 5,342,908 A | 8/1994 | Osman | |
| 5,344,579 A | 9/1994 | Ohtani et al. | |
| 5,372,735 A | 12/1994 | Ohtani et al. | |
| 5,393,309 A | 2/1995 | Cherpeck | |
| 5,441,656 A | 8/1995 | Ohtani et al. | |
| 5,454,964 A | 10/1995 | Blackborow et al. | |
| 5,590,716 A * | 1/1997 | Mansfield | ............... 166/302 |
| 5,700,765 A | 12/1997 | Barnes et al. | |
| 5,858,177 A * | 1/1999 | Morris | ............... 203/26 |
| 5,882,505 A | 3/1999 | Wittenbrink et al. | |
| 6,013,171 A | 1/2000 | Cook et al. | |
| 6,080,301 A | 6/2000 | Berlowitz et al. | |
| 6,096,940 A | 8/2000 | Wittenbrink et al. | |
| 6,103,099 A | 8/2000 | Wittenbrink et al. | |
| 6,165,949 A | 12/2000 | Berlowitz et al. | |
| 6,180,575 B1 | 1/2001 | Nipe | |
| 6,362,136 B1 | 3/2002 | Richardson et al. | |
| 2002/0151441 A1 | 10/2002 | Srinivasan et al. | |

FOREIGN PATENT DOCUMENTS

| | | |
|---|---|---|
| EP | 0 020 037 | 12/1980 |
| WO | 9813443 | 4/1998 |

OTHER PUBLICATIONS

Bernard Loev, Sulfolane Derivatives, Journal of Org Chem. Nov. 1961, vol. 26, No. 11, American Chemical Society, Easton, US.

* cited by examiner

*Primary Examiner*—Bernard Dentz
*Assistant Examiner*—David E Gallis
(74) *Attorney, Agent, or Firm*—Luedeka, Neely & Graham, P.C.

(57) ABSTRACT

A method of making 3-alkoxytetraalkylene sulfone. The method includes mixing an alcohol and a catalyst to form a first mixture. Alkadiene sulfone is reacted with the first mixture to form a reaction product. The reaction product is contacted with water at conditions sufficient to provide an organic phase and an inorganic phase. Subsequent to contacting the reaction product with water, the organic phase and inorganic phase are separated from one another.

45 Claims, No Drawings

SEAL SWELL AGENT AND PROCESS THEREFOR

FIELD

The present disclosure relates to seal swelling agents and in particular to improved seal swelling agents, methods for their production, and uses therefor.

BACKGROUND

Seal swelling agents, such as esters, adipates, sebacates, azeealates, phthalates, sulfones, alcohols, alkylbenzenes, substituted sulfolanes, aromatics, or mineral oils, are introduced into functional fluids used in machinery in order to minimize seal shrinkage. Examples of functional fluids include automatic transmission fluids, hydraulic fluids, lubricants, and other fluids used in heat exchange equipment. Seal swelling agents are used to address the problem of seal shrinkage, wherein seals shrink and ultimately cause functional fluid leakage. When the functional fluid is lost, machinery can slowly breakdown or stop working altogether.

A number of seal swelling agents are known in the art including those listed above. One seal swelling agent of particular interest is a substituted sulfolane as described for example in U.S. Pat. No. 4,029,588 to Koch, the disclosure of which is incorporated herein by reference. However, substituted sulfolanes often include undesirable impurities. These impurities include water, catalyst, unreacted sulfolene, and/or unreacted alcohol. Water has a particularly adverse effect on elastomeric seals commonly used in lubricant applications.

Because of the impurity levels in substituted sulfolanes, and an inability to remove the impurities economically, many companies have chosen to use other seal swell agent additives. One such compound is a naphthalene depleted aromatic compound commercially available from Exxon Mobil Corporation under the trade name AROMATIC 200 ND (hereinafter, "200 ND"). However, the treat rate for 200 ND is relatively high and 200 ND emits an unpleasant odor. Therefore, there is a continuing need to find cost-effective ways to maximize the positive aspects of suitable seal swell agents while minimizing undesirable characteristics of the agents.

SUMMARY OF THE EMBODIMENTS

With regard to the above, there is provided a method of making 3-alkoxytetraalkylene sulfone. The method includes mixing an alcohol and a catalyst to form a first mixture. Alkadiene sulfone is reacted with the first mixture to form a reaction product. The reaction product is contacted with water at conditions sufficient to provide an organic phase and an inorganic phase. Subsequent to contacting the reaction product with water, the organic phase and inorganic phase are separated from one another.

In another embodiment, there is provided a lubricant additive concentrate including a seal swelling agent of the formula:

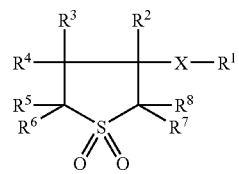

where $R^1$ is selected from an alkyl and an alkylene group containing from about 4 to about 30 carbon atoms, X is selected from a group consisting of O and S, and each of the $R^2$ to $R^8$ may be selected from H and an alkyl group containing from about 1 to about 4 carbon atoms, the foregoing being derived from butadiene sulfone and an alcohol containing from about 4 to about 30 carbon atoms, wherein the seal swelling agent contains less than about 500 ppm catalyst.

Accordingly, there is provided an improved process for making seal swelling agents, particularly substituted sulfolanes, wherein impurity levels in the sulfolane products are reduced to suitable levels without undertaking costly or complicated purification techniques. While substituted sulfolanes have been used as seal swelling agents in lubricant formulations, their effectiveness has been limited due to unacceptably high levels of impurities in the agents which adversely affect modern day elastomeric seal materials. However, the embodiments described herein enable use of substituted sulfolanes that are more compatible with elastomeric seal materials.

DETAILED DESCRIPTION OF EMBODIMENTS

As used herein, the term "hydrocarbyl substituent" or "hydrocarbyl group" is used in its ordinary sense, which is well-known to those skilled in the art. Specifically, it refers to a group having a carbon atom directly attached to the remainder of a molecule and having a predominantly hydrocarbon character. Examples of hydrocarbyl groups include:

(1) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form an alicyclic radical);

(2) substituted hydrocarbon substituents, that is, substituents containing non-hydrocarbon groups which, in the context of the description herein, do not alter the predominantly hydrocarbon substituent (e.g., halo (especially chloro and fluoro), hydroxy, alkoxy, mercapto, alkylmercapto, nitro, nitroso, and sulfoxy);

(3) hetero-substituents, that is, substituents which, while having a predominantly hydrocarbon character, in the context of this description, contain other than carbon in a ring or chain otherwise composed of carbon atoms. Hetero-atoms include sulfur, oxygen, nitrogen, and encompass substituents such as pyridyl, furyl, thienyl and imidazolyl. In general, no more than two, as a further example, no more than one, non-hydrocarbon substituent will be present for every ten carbon atoms in the hydrocarbyl group; typically, there will be one non-hydrocarbon substituent in the hydrocarbyl group.

As power transmission fluids, such as vehicle transmission fluids, operate under increasingly severe conditions, the oils used to lubricate those transmissions should be formulated to endure higher temperatures and pressures. Accordingly, such transmission fluids are formulated with a base oil and certain additives that improve the performance of the fluids. Unfortunately, there is often interaction between components of the fluids and the power transmission components that reduce the effectiveness of the fluids and/or are less compatible with modern materials used in the power transmission components. In particular, seal materials used in the power transmission components are susceptible to shrinkage caused by impurities in the fluids. In order to avoid compatibility problems, formulators have selected more costly components to include in the power transmission fluids. For example, substituted sulfolanes have been replaced with a naphthalene depleted aromatic compound as described above because the water and impurity levels in substituted sulfolanes are often too high and difficult to remove. Excess water in the additives may also reduce the solubility of some of the components of the additive causing undesirable precipitation of components of the additive.

Improved Power Transmission Component

Despite the current trend to use alternative seal swelling agents in power transmission fluids, improvements in a process for making substituted sulfolanes have been found to yield products that are less costly to manufacture yet contain lower levels of impurities than conventionally made products. In particular, it has been found, quite unexpectedly, that organic and inorganic phases resulting from a reaction between butadiene sulfone and an alcohol, such as iso-decyl alcohol, will demulsify at a temperature within a relatively narrow range, typically from about 80° C. to about 85° C. Demulsification in this temperature range enables separation of polar and non-polar species from one another in a reaction product mixture. Consequently, the desired reaction product may be isolated and purified to a greater degree using a simplified separation technique as described in more detail below. The improved substituted sulfolane reaction product may be used as a seal swelling agent in, for example, power transmission fluids, thereby minimizing the shrinkage of seals in contact with the fluids.

In accordance with embodiments of the disclosure, the substituted sulfolane product may be represented by the formula:

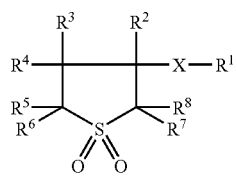

where $R^1$ is selected from an alkyl and an alkylene group containing from about 4 to about 30 carbon atoms, for example, a branched alkyl or alkylene group containing from about 8 to about 16 carbon atoms, X is selected from a group consisting of O and S, and each of the $R^2$ to $R^8$ may be selected from H and an alkyl group containing from about 1 to about 4 carbon atoms, the foregoing being derived from butadiene sulfone and an alcohol containing from about 4 to about 30 carbon atoms, as a further example, from about 8 to about 16 carbon atoms.

Suitable alcohols which may be reacted with butadiene sulfone include, but are not limited to, butyl, amyl, hexyl, octyl, decyl, dodecyl, tetradecyl, hexadecyl, octadecyl, eicosyl, triacontanyl, butenyl, dodecenyl, phenyl, naphthyl, tolyl, dodecylphenyl, tetrapropene-alkylated phenyl, phenylethyl, cyclohexyl, methylcyclohexyl alcohols and isomers thereof. Alkyl radicals for $R^1$ may have from about 4 to about 30 carbon atoms and, as a further example, from about 8 to about 18 carbon atoms.

In one embodiment of a reaction process for making substituted sulfolanes according to the disclosure, a $C_8$-$C_{16}$ alkyl alcohol ($R^1$) is added to a reaction vessel along with a suitable inorganic catalyst, i.e., potassium hydroxide (KOH). The components in the reaction vessel are stirred and heated to about 75° C. for a period of time sufficient to substantially dissolve all of the KOH and form a reaction mass. The reaction mass is then cooled to room temperature and butadiene sulfone is added to the reaction vessel to form a reaction mixture. The subsequent chemical reaction forming a substituted sulfolane reaction product is depicted below as follows:

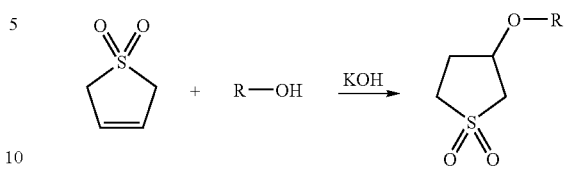

Reaction efficiency may be increased by slight heating and stirring of the reaction vessel contents during the reaction between the sulfone and alcohol.

The amount of alcohol to mole of sulfone in the reaction mixture may range from about 0.5:1 to about 2:1 on a mole basis. The amount of catalyst per mole of sulfone or alcohol in the reaction mixture is in a catalytic amount and may range from about 0.01:1 to about 0.1:1 on a mole basis.

After the reaction has substantially concluded, water is added to the reaction product in the reaction vessel. The amount of water added to the reaction vessel typically ranges from about 3 to about 10 times the amount of sulfone or alcohol in the reaction vessel on a mole basis. The water causes an emulsion to form in the reaction vessel between an organic phase containing the substituted sulfolane produce and an aqueous phase containing the catalyst.

Upon heating the reaction vessel contents to a temperature ranging from about 80° C. and about 85° C. while stirring the reaction product, the emulsion is broken thereby providing separable aqueous and organic phases. The aqueous and organic phases may be separated from one another upon settling of the reaction vessel contents using conventional phase separation techniques, such as physically draining the aqueous phase from the bottom of the vessel.

To further ensure substantial water removal from the reaction product, the reaction vessel contents may be stripped using a vacuum of about 28 inches of Hg at the temperature ranging from about 80° C. and about 85° C. The resulting product, substantially free of the aqueous phase, may then be filtered using 0.5 wt. % filter body aid and from about 2 to about 4 wt % filter precoat material based on the weight of the reaction product.

The embodiment described above yields a substituted sulfolane seal swell agent product having a residual water content of about 1500 ppm or less, a sulfur dioxide content of about 200 ppm or less, and a potassium content of about 500 ppm or less.

In order to further minimize the residual impurity levels in the reaction product, a second water addition and phase separation step may be conducted before the vacuum stripping and filtration steps using the same procedure described above. The second water addition step and subsequent phase separation may be effective to provide a sulfur dioxide impurity content of less than about 1 ppm and a potassium content of less than about 5 ppm in the reaction product.

In a further embodiment, some or all of the water separated from the reaction vessel in the phase separation step may be recycled and used in a subsequent batch in an initial water addition step for purifying the product. For example, the inorganic phase removed from a first batch of reaction product after the second water addition step may be used as the first water addition step in a subsequent batch of reaction product. Accordingly, this embodiment may be useful for conserving water and minimizing waste streams from the process.

In yet another embodiment, the reaction product is made as described above by reacting an alcohol and sulfone in the presence of a catalyst. However, prior to the water addition step, an inorganic acid, such as sulfuric acid ($H_2SO_4$), may be added to neutralize the KOH catalyst upon completion of the reaction between the alcohol and sulfone.

By way of example, a reaction mixture may be formed, and the catalyst neutralized and impurities removed by use of reactants and water in the amounts listed in the table. These values are meant to be approximations and are not intended to limit the disclosure.

TABLE 1

| Component | Weight percent of total |
|---|---|
| Iso-decyl alcohol | 41.14 |
| KOH | 0.66 |
| Butadiene sulfone | 31.32 |
| Water (per water addition step) | 26.54 |
| Sulfuric acid | 0.33 |

In the following examples, substituted sulfolane products are made by processes according to the disclosed embodiments and by alternative processes. The examples are not intended to limit the invention in any way.

EXAMPLE 1

A seal swelling agent according to the disclosure was made in a one-liter 3-neck resin flask with bottom outlet. The flask was equipped with an agitator, an addition funnel, a thermometer, a temperature controller, and a condenser. For accurate weight measurements, the empty reaction flask was weighed with the stirrer and thermometer before proceeding with the reaction. The first step of the process included charging 155 grams of an iso-decyl alcohol into the reaction flask. The next step included charging 2.5 grams of solid KOH into the reaction flask while stirring the contents of the flask. The reaction flask contents were then heated to about 75° C. The heating step was continued for at least one hour to ensure that substantially all of the KOH had been dissolved in the alcohol. The alcohol was then cooled to room temperature.

The next step included charging 118 grams of solid butadiene sulfone into the reaction flask. The reaction flask contents were then stirred at room temperature until the entire solid was reacted with substantially no solid remained in the reaction flask. The reaction flask contents were then heated to about 35° C. to ensure that substantially all of the butadiene sulfone had reacted. When the temperature of the reaction flask contents reached 35° C., 100 grams of water was charged to the reaction flask. The reaction flask contents were then further heated to between about 80° and about 85° C. while stirring the reaction flask contents. Once the reaction flask contents reached between about 80° C. and about 85° C., the stirring was terminated and the reaction flask contents were allowed to settle within that temperature range for about thirty minutes. The bottom inorganic (water) phase was then removed from the flask and discarded. The inorganic phase removal step continued until the organic phase was seen.

After removing the inorganic phase from the flask, 100 grams of additional water were charged to the reaction flask. The reaction flask contents were again heated to between about 80° C. and about 85° C. while stirring the contents. Once the contents of the flask reached between about 80° C. and about 85° C., the stirring was terminated and the reaction flask contents were allowed to settle for about thirty minutes. Again, the inorganic (water) phase was removed from the flask and discarded. Then the remaining organic phase in the flask was stripped at between about 80° C. and about 85° C. under a vacuum of 28 inches of Hg for about one hour. The temperature was then lowered to about 50° C. and nitrogen sparging was initiated for about thirty minutes. Filter aid (0.5 wt %) was added to the reaction flask as a body aid. The flask contents were then filtered using 10 grams of filter pre-coat material. The analytical results from the filtered product in Example 1 are shown in the following table.

TABLE 2

| Measured Quantity | |
|---|---|
| Water in ppm | 1524 |
| Potassium in ppm | 0 |
| Specific gravity at 15.6° C. | 1.03 |
| Appearance | Bright and clear yellow liquid |
| Color, ASTM | 0.5 |
| Sulfur in weight % | 11.5 |
| Flash Point, ° C. (PMCC) | 110 min. |
| Viscosity at 40° C., in cSt | 25 |
| FT-IR | matches standard |
| Unreacted Sulfolene in weight % | <0.75 |
| Sulfur dioxide in ppm | <1.0 |

By contrast to the above example, commercially available substituted sulfolane products typically contain from about 4000 to about 7000 ppm water and more than 100 ppm sulfur dioxide.

EXAMPLE 2

A product was prepared according to the procedure of Example 1 with the exception that only one water wash was applied instead of two water washes when the reaction was complete. The resulting filtered product had identical characteristics as that of example 1 (as shown in Table 2) with the exception that the product had a much higher potassium content (382 ppm K).

EXAMPLE 3

A seal swelling agent according to the disclosure was made in a one-liter 3-neck resin flask with bottom outlet. The flask was equipped with an agitator, an addition funnel, a thermometer, a temperature controller, and a condenser. For accurate weight measurements, the empty reaction flask was weighed with the stirrer and thermometer before proceeding with the reaction. The first step of the process included charging 119.6 grams of an iso-decyl alcohol into the reaction flask. The next step included charging 1.9 grams of solid KOH into the reaction flask while stirring the contents of the flask. The reaction flask contents were then heated to about 75° C. The heating step was continued for at least one hour to ensure that substantially all of the KOH had been dissolved in the alcohol. The reaction flask contents were then cooled to about 25° C.

When the reaction flask contents reached about 25° C., the stirring was terminated and about 91.1 grams of butadiene sulfone were charged into the reaction flask. The reaction flask was then sealed and the contents were stirred for about one and a half hours. After about one hour of stirring, a temperature increase of the reaction flask contents to about 40° C. was observed. In the final half hour, the temperature of the reaction flask contents decreased to about 35° C. A sample of the reaction flask contents was taken and examined to ensure that all of the solid sulfone had dissolved.

After all of the solids had reacted, about 77.2 grams of water and about 77.2 grams of heptane were charged to the reaction flask. The reaction flask contents were then heated to about 50° C. and stirred for 15 minutes. The reaction flask contents were then allowed to settle for 45 minutes. The bottom inorganic (water) layer was then removed from the bottom valve of the reaction flask until the organic layer was seen. The reaction flask was then configured for stripping the reaction flask contents at atmospheric pressure. The reaction flask contents were then heated to about 90° C. Heptane began to strip from the reaction flask contents at about 78° C. When the reaction flask contents reached about 90° C., the contents were held at 90° C. for about 10 minutes.

The contents of the reaction flask were stripped until substantially all of the remaining heptane and residual water were removed. The initial stripping was performed at about 90° C. Additional stripping was conducted at about 85° C. and 26 inches of water vacuum for about 45 minutes. Nitrogen was then introduced to the reaction flask in order to break the vacuum.

A sample of the reaction flask contents was taken to determine whether the amount of water present was less than 300 ppm. When analysis of the reaction flask contents showed that the water content was less than 300 ppm, the stripping process was terminated. Before filtering the reaction product, the reaction flask contents were charged with 1 gram of filter aid and stirred for about 15 minutes. The analytical results from the filtered product in Example 3 are shown in the following table.

TABLE 3

| Measured Quantity | |
|---|---|
| Water in ppm | 1540 |
| Potassium in ppm | 5 |
| Specific gravity at 15.6° C. | 1.03 |
| Appearance | Bright and clear yellow liquid |
| Color, ASTM | 0.5 |
| Sulfur in weight % | 11.4 |
| Flash Point, ° C. (PMCC) | 110 min. |
| Viscosity at 40° C., in cSt | 24 |
| FT-IR | matches standard |
| Unreacted Sulfolene in weight % | <0.75 |
| Sulfur dioxide in ppm | <1.0 |

While the foregoing process provides a product similar to the product in example 1, the additional steps of using heptane and removing the heptane from the product complicates the process.

EXAMPLE 4

A product was prepared according to the procedure of Example 1 with the exception that, upon completion of the reaction, 20% concentration sulfuric acid (H$_2$SO$_4$) was charged to the reaction flask to neutralize the KOH. The sulfuric acid was added in a quantity equal to the molar content of the KOH. The resulting filtered product characteristics are shown in the following table.

TABLE 4

| Measured Quantity | |
|---|---|
| Water in ppm | 234 |
| Potassium in ppm | 83 |
| Specific gravity at 15.6° C. | 1.03 |
| Appearance | Clear to slightly hazy yellow liquid |
| Color, ASTM | 1.0 |
| Sulfur in weight % | 10.97 |
| Flash Point, ° C. (PMCC) | 110 min. |

TABLE 4-continued

| Measured Quantity | |
|---|---|
| Viscosity at 40° C., in cSt | 27.32 |
| FT-IR | matches standard |

Like example 3, the use of sulfuric acid provides a suitable product, however, the process is more complicated as it is difficult to neutralize all of the KOH catalyst without introducing excess acid into the product.

EXAMPLE 5

A product was prepared according to the procedure of Example 1 or Example 3 with the exception that no solvent (water or heptane) was added to the batch. Instead, two different grades of magnesium silicate powder available from Dallas Group of America, Inc. of Whitehouse, N.J. under the trade name MAGNESOL (about 6 wt % total) were added to the reaction flask contents after completion of the reaction to absorb the catalyst before filtration. The resulting filtered product characteristics are shown in the following table.

TABLE 5

| Measured Quantity | MAGNESOL GRADE 30/40 | MAGNESOL HMR-LS |
|---|---|---|
| Water in ppm | 5604 | 1833 |
| Potassium in ppm | 480 | 480 |
| Specific gravity at 15.6° C. | 1.03 | 1.09 |
| Appearance | Clear to slightly hazy yellow liquid | Clear to slightly hazy yellow liquid |
| Color, ASTM | 1.0 | 1.5 |
| Sulfur in weight % | 12.05 | 11.86 |
| Flash Point, ° C. (PMCC) | 110 min. | 110 min. |
| Viscosity at 40° C., in cSt | 22.61 | 24.39 |
| FT-IR | Matches standard | Matches standard |
| Sulfur dioxide in ppm | 0 | 0 |

The process of using MAGNESOL HMR-LS provides results similar to example 1, however as with examples 3 and 4, the process is more complicated and requires additional steps. It is also expected that the products made by this example have much higher potassium contents than the product of example 1.

EXAMPLE 6

A product was prepared according to the procedure of Example 1 with the exception that the water used for the first wash was recycled and used for the second wash. The resulting filtered product characteristics are shown in the following table.

TABLE 6

| Measured Quantity | |
|---|---|
| Water in ppm | 940 |
| Specific gravity at 15.6° C. | 1.03 |
| Appearance | Bright and clear yellow liquid |
| Color, ASTM | 1.0 |
| Sulfur in weight % | 11.58 |
| Flash Point, ° C. (PMCC) | 110 min. |

TABLE 6-continued

| Measured Quantity | |
| --- | --- |
| Viscosity at 40° C., in cSt | 27.24 |
| FT-IR | matches standard |

This example demonstrated a method for recovering product from a second wash step of a previous batch while providing a purified product. The following table is a composite of the results from the foregoing examples.

TABLE 7

| Measured Quantity | Example 1 | Example 2 | Example 3 | Example 4 | Example 5 | Example 5 |
| --- | --- | --- | --- | --- | --- | --- |
| Water in ppm | 1524 | 1524 | 1540 | 234 | 1833 | 5604 |
| Potassium in ppm | 0 | 382 | 5 | 83 | 480 | 480 |
| Specific gravity at 15.6° C. | 1.03 | 1.03 | 1.03 | 1.03 | 1.03 | 1.09 |
| Appearance | Bright and clear yellow liquid | Bright and clear yellow liquid | Bright and clear yellow liquid | Clear to slightly hazy yellow liquid | Clear to slightly hazy yellow liquid | Clear to slightly hazy yellow liquid |
| Color, ASTM | 0.5 | 0.5 | 0.5 | 1.0 | 1.0 | 1.5 |
| Sulfur in weight % | 11.5 | 11.5 | 111.4 | 10.97 | 11.86 | 12.05 |
| Flash Point, ° C. (PMCC) | 110 min. | 110 min. | 110 min. | 110 min. | 110 min. | 110 min. |
| Viscosity at 40° C., in cSt | 25 | 25 | 24 | 27.32 | 22.61 | 24.39 |
| Sulfur dioxide in ppm | <1 | <1 | <1 | 0 | 0 | 0 |

As shown by the foregoing examples a superior substituted sulfolane product may be made by using two water washes according to examples 1 and 6 without the use of additional or complicated purification steps.

Substituted sulfolane products made according to the disclosure may be incorporated in oleaginous formulations in conventional amounts. For example, power transmission fluids, such as automatic transmission fluids, may contain from about 0.1 to about 10 weight percent of the substituted sulfolane product based on the total weight of the composition. The oleaginous formulations may be used, for example, in automotive applications, such as automatic transmissions, and in other power transmission applications. Such oleaginous fluids typically include, but are not limited to, a base oil, ashless dispersants, friction modifiers, viscosity index improvers, detergents, antioxidants, extreme pressure additives, corrosion inhibitors, antiwear additives, metal deactivators, antifoamants, pour point depressants, air entrainment additives, and/or metallic detergents.

Base Oil

Base oils suitable for use in formulating oleaginous compositions according to the disclosure may be selected from any of the synthetic or natural oils or mixtures thereof. Natural oils include animal oils and vegetable oils (e.g., castor oil, lard oil) as well as mineral lubricating oils such as liquid petroleum oils and solvent treated or acid-treated mineral lubricating oils of the paraffinic, naphthenic or mixed paraffinic-naphthenic types. Oils derived from coal or shale are also suitable. The base oil typically has a viscosity of about 2 to about 15 cSt and, as a further example, about 2 to about 10 cSt at 100° C.

The synthetic base oils include alkyl esters of dicarboxylic acids, polyglycols and alcohols, poly-alpha-olefins, including polybutenes, alkyl benzenes, organic esters of phosphoric acids, and polysilicone oils. Synthetic oils include hydrocarbon oils such as polymerized and interpolymerized olefins (e.g., polybutylenes, polypropylenes, propylene isobutylene copolymers, etc.); poly(1-hexenes), poly-(1-octenes), poly(1-decenes), etc. and mixtures thereof; alkylbenzenes (e.g., dodecylbenzenes, tetradecylbenzenes, di-nonylbenzenes, di-(2-ethylhexyl)benzenes, etc.); polyphenyls (e.g., biphenyls, terphenyl, alkylated polyphenyls, etc.); alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc., constitute another class of known synthetic oils that may be used. Such oils are exemplified by the oils prepared through polymerization of ethylene oxide or propylene oxide, the alkyl and aryl ethers of these polyoxyalkylene polymers (e.g., methyl-polyisopropylene glycol ether having an average molecular weight of about 1000, diphenyl ether of polyethylene glycol having a molecular weight of about 500-1000, diethyl ether of polypropylene glycol having a molecular weight of about 1000-1500, etc.) or mono- and polycarboxylic esters thereof, for example, the acetic acid esters, mixed $C_{3-8}$ fatty acid esters, or the $C_{13}$ Oxo acid diester of tetraethylene glycol.

Another class of synthetic oils that may be used includes the esters of dicarboxylic acids (e.g., phtbalic acid, succinic acid, alkyl succinic acids, alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.) Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include those made from $C_5$ to $C_{12}$ monocarboxylic acids and polyols and polyol ethers such as neopentyl glycol, trimethylol propane, pentaerythritol, dipentaerythritol, tripentaerythritol, etc.

Hence, the base oil used which may be used to make the oleaginous compositions as described herein may be selected from any of the base oils in Groups I-V as specified in the American Petroleum Institute (API) Base Oil Interchangeability Guidelines. Such base oil groups are as follows:

| Base Oil Group[1] | Sulfur (wt. %) | | Saturates (wt. %) | Viscosity Index |
|---|---|---|---|---|
| Group I | >0.03 | and/or | <90 | 80 to 120 |
| Group II | ≦0.03 | And | ≧90 | 80 to 120 |
| Group III | ≦0.03 | And | ≧90 | ≧120 |
| Group IV | | all polyalphaolefins (PAOs) | | |
| Group V | | all others not included in Groups I-IV | | |

[1]Groups I-III are mineral oil base stocks.

As set forth above, the base oil may be a poly-alpha-olefin (PAO). Typically, the poly-alpha-olefins are derived from monomers having from about 4 to about 30, or from about 4 to about 20, or from about 6 to about 16 carbon atoms. Examples of useful PAOs include those derived from octene, decene, mixtures thereof, and the like. PAOs may have a viscosity of from about 2 to about 15, or from about 3 to about 12, or from about 4 to about 8 cSt at 100° C. Examples of PAOs include 4 cSt at 100° C. poly-alpha-olefins, 6 cSt at 100° C. poly-alpha-olefins, and mixtures thereof. Mixtures of mineral oil with the foregoing poly-alpha-olefins may be used.

The base oil may be an oil derived from Fischer-Tropsch synthesized hydrocarbons, a gas-to-liquid stock, and/or a mixture thereof. Fischer-Tropsch synthesized hydrocarbons are made from synthesis gas containing $H_2$ and CO using a Fischer-Tropsch catalyst. Such hydrocarbons typically require further processing in order to be useful as the base oil. For example, the hydrocarbons may be hydroisomerized using processes disclosed in U.S. Pat. Nos. 6,103,099 or 6,180,575; hydrocracked and hydroisomerized using processes disclosed in U.S. Pat. Nos. 4,943,672 or 6,096,940; dewaxed using processes disclosed in U.S. Pat. No. 5,882,505; or hydroisomerized and dewaxed using processes disclosed in U.S. Pat. Nos. 6,013,171; 6,080,301; or 6,165,949.

Unrefined, refined and rerefined oils, either natural or synthetic (as well as mixtures of two or more of any of these) of the type disclosed hereinabove can be used in the base oils. Unrefined oils are those obtained directly from a natural or synthetic source without further purification treatment. For example, a shale oil obtained directly from retorting operations, a petroleum oil obtained directly from primary distillation or ester oil obtained directly from an esterification process and used without further treatment would be an unrefined oil. Refined oils are similar to the unrefined oils except they have been further treated in one or more purification steps to improve one or more properties. Many such purification techniques are known to those skilled in the art such as solvent extraction, secondary distillation, acid or base extraction, filtration, percolation, etc. Rerefined oils are obtained by processes similar to those used to obtain refined oils applied to refined oils which have been already used in service. Such rerefined oils are also known as reclaimed or reprocessed oils and often are additionally processed by techniques directed to removal of spent additives, contaminants, and oil breakdown products.

Additives used in formulating the compositions described herein can be blended into the base oil individually or in various sub-combinations. For example, all of the components may be blended concurrently using an additive concentrate (i.e., additives plus a diluent, such as a hydrocarbon solvent). The use of an additive concentrate takes advantage of the mutual compatibility afforded by the combination of ingredients when in the form of an additive concentrate. Also, the use of a concentrate reduces blending time and lessens the possibility of blending errors.

The power transmission fluids disclosed herein may include fluids suitable for any power transmitting application, such as a step automatic transmission or a manual transmission. Further, the power transmission fluids of the present invention are suitable for use in transmissions with a slipping torque converter, a lock-up torque converter, a starting clutch, and/or one or more shifting clutches. Such transmissions include four-, five-, six-, and seven-speed transmissions, and continuously variable transmissions (chain, belt, or disk type). They may also be used in manual transmissions, including automated manual and dual-clutch transmissions.

At numerous places throughout this specification, reference has been made to a number of U.S. Patents. All such cited documents are expressly incorporated in full into this disclosure as if fully set forth herein.

Other embodiments of the present disclosure will be apparent to those skilled in the art from consideration of the specification and practice of the disclosed embodiments herein. As used throughout the specification and claims, "a" and/or "an" may refer to one or more than one. Unless otherwise indicated, all numbers expressing quantities of ingredients, properties such as molecular weight, percent, ratio, reaction conditions, and so forth used in the specification and claims are to be understood as being modified in all instances by the term "about." Accordingly, unless indicated to the contrary, the numerical parameters set forth in the specification and claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. It is intended that the specification and examples be considered as exemplary only, with a true scope and spirit of the disclosed embodiments being indicated by the following claims.

The invention claimed is:

1. A method of making 3-alkoxytetraalkylene sulfone comprising:
    mixing an alcohol and a catalyst to form a first mixture;
    reacting alkadiene sulfone with the first mixture to form a reaction product;
    contacting the reaction product with water and heating the reaction product and water to a temperature sufficient to provide an organic phase and an inorganic phase; and
    separating the organic phase and inorganic phase from one another,
wherein the organic phase contains less than about 2000 ppm water.

2. The method of claim 1, wherein the organic phase contains less than about 0.75 percent weight of unreacted alkadiene sulfone.

3. The method of claim 1, wherein the organic phase contains less than about 1 ppm $SO_2$.

4. The method of claim 1, wherein the organic phase contains less than about 12 percent weight of sulfur.

5. The method of claim 1, wherein the contacting step comprises: contacting the reaction product with water at a temperature ranging from about 80° C. to about 85° C. to provide the organic phase and the inorganic phase.

6. The method of claim 1, wherein the contacting step comprises: contacting the reaction product with water at a temperature ranging from about 80° C. to about 85° C. to provide a first organic phase and a first inorganic phase; separating the first inorganic phase and first organic phase from one another; contacting the first organic phase with water at a temperature ranging from about 80° C. to about 85° C. to provide a second organic phase and a second inorganic phase; and separating the second organic phase and second inorganic phase from one another to provide a purified 3-alkoxytetraalkylene sulfone product.

7. The method of claim 6, wherein the sulfone product has a potassium content of form about 0 to about 2 ppm.

8. The method of claim 1, wherein the alkadiene sulfone comprises butadiene sulfone.

9. The method of claim 1, wherein the alkadiene sulfone comprises sulfolene.

10. The method of claim 9, wherein the 3-alkoxytetraalkylene sulfone comprises 3-alkoxytetramethylene sulfone.

11. The method of claim 10, wherein the alkoxy groups of the 3-alkoxytetramethylene sulfone contain from about 4 to about 30 carbon atoms.

12. The method of claim 1, wherein the alcohol contains from about 4 to about 30 carbon atoms.

13. The method of claim 12, wherein the alcohol contains from about 8 to about 16 carbon atoms.

14. The method of claim 1, wherein the alcohol is selected from the group consisting of butyl, amyl, hexyl, octyl, decyl, dodecyl, tetradecyl, hexadecyl, octadecyl, eicosyl, triacontanyl, butenyl, dodecenyl, phenyl, naphthyl, tolyl, dodecylphenyl, tetrapropene-alkylated phenyl, phenylethyl, cyclohexyl, methylcyclohexyl alcohols and isomers thereof.

15. The method of claim 1, wherein the alcohol is iso-decyl alcohol.

16. The method of claim 1, wherein the ratio of alcohol to sulfone ranges from about 0.5:1 to about 2:1 on a mole basis.

17. The method of claim 16, wherein the ratio of alcohol to sulfone ranges from about 0.01:1 to about 0.1:1 on a mole basis.

18. In a process of making 3-alkoxytetraalkylene sulfone wherein an alcohol and alkadiene sulfone are reacted in the presence of a catalyst to form a reaction product, an improvement comprising: adding water to the reaction product to form a first mixture; heating the first mixture to a sufficient temperature to form a first organic phase and a first inorganic phase; separating the first organic phase and first inorganic phase from one another to provide a 3-alkoxytetraalkylene sulfone product having a reduced impurity level.

19. The improvement of claim 18, wherein the heating step comprises: heating the first mixture to a temperature ranging from about 80° C. to about 85° C. to form the first organic phase and the first inorganic phase.

20. The improvement of claim 18, further comprising adding water to the first organic phase to form a second mixture; heating the second mixture to a sufficient temperature to provide a second organic phase and a second inorganic phase; and separating the second inorganic phase and second organic phase from one another, wherein the impurity level of catalyst in the organic phase ranges from about 0 to about 5 ppm.

21. The improvement of claim 20, wherein the heating step comprises: heating the second mixture to a temperature ranging from about 80° C. to about 85° C. to provide the second organic phase and the second inorganic phase.

22. The improvement of claim 18, wherein the second organic phase contains less than about 2000 ppm water.

23. The improvement of claim 18, wherein the second organic phase contains less than about 0.75 percent weight of unreacted alkadiene sulfone.

24. The improvement of claim 18, wherein the second organic phase contains less than about 1 ppm $SO_2$.

25. The improvement of claim 18, wherein the second organic phase contains less than about 12 percent weight of sulfur.

26. The improvement of claim 18, further comprising: adding water to the 3-alkoxytetraalkylene sulfone product to form a second mixture; heating the second mixture to a sufficient temperature to provide a second organic phase and a second inorganic phase; and separating the second organic phase and second inorganic phase from one another.

27. The improvement of claim 26, wherein the heating step comprises: heating the second mixture to a temperature ranging from about 80° C. to about 85° C. to provide the second organic phase and the second inorganic phase.

28. The improvement of claim 18, wherein the alkadiene sulfone comprises butadiene sulfone.

29. The improvement of claim 18, wherein the alkadiene sulfone comprises sulfolene.

30. The improvement of claim 29, wherein the 3-alkoxytetraalkylene sulfone comprises 3-alkoxytetramethylene sulfone.

31. The improvement of claim 30, wherein the alkoxy groups of the 3-alkoxytetramethylene sulfone contain from about 4 to about 30 carbon atoms.

32. The improvement of claim 18, wherein the alcohol contains from about 4 to about 30 carbon atoms.

33. The improvement of claim 32, wherein the alcohol contains from about 8 to about 16 carbon atoms.

34. The improvement of claim 18, wherein the alcohol is selected from the group consisting of butyl, amyl, hexyl, octyl, decyl, dodecyl, tetradecyl, hexadecyl, octadecyl, eicosyl, triacontanyl, butenyl, dodecenyl, phenyl, naphthyl, tolyl, dodecylphenyl, tetrapropene-alkylated phenyl, phenylethyl, cyclohexyl, methylcyclohexyl alcohols and isomers thereof.

35. The improvement of claim 18, wherein the alcohol is iso-decyl alcohol.

36. The improvement of claim 18, wherein the ratio of alcohol to sulfone ranges from about 0.5:1 to about 2:1 on a mole basis.

37. The improvement of claim 36, wherein the ratio of alcohol to sulfone ranges from about 0.01:1 to about 0.1:1 on a mole basis.

38. A lubricant composition comprising a base oil and the sulfone product of claim 18 wherein the sulfone product, as made, contains less than 2000 ppm water.

39. The lubricant composition of claim 38, wherein the sulfone product is present in the composition in an amount ranging from about 0.1 to about 10.0 percent by weight.

40. A vehicle transmission fluid comprising the sulfone product of claim 18 wherein the sulfone product, as made, contains less than 2000 ppm water.

41. An additive concentrate for a transmission fluid, the additive concentrate comprising from about 0.1 to about 10.0 percent by weight of the sulfone product of claim 18.

42. A lubricant additive concentrate comprising a seal swelling agent of the formula:

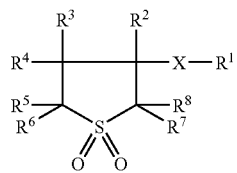

where $R^1$ is selected from an alkyl and an alkylene group containing from about 4 to about 30 carbon atoms, X is O, and each of the $R^2$ to $R^8$ may be selected from H and an alkyl group containing from about 1 to about 4 carbon atoms, the foregoing being derived from butadiene sulfone and an alcohol containing from about 4 to about 30 carbon atoms, wherein the seal swelling agent, as made, contains less than about 5 ppm catalyst and less than 2000 ppm water.

43. The additive concentrate of claim 42, wherein the seal swelling agent contains less than about 0.75 percent weight of unreacted alkadiene sulfone.

44. The additive concentrate of claim 42, wherein the seal swelling agent contains less than about 1 ppm $SO_2$.

45. The additive concentrate of claim 42, wherein the seal swelling agent contains less than about 12 percent weight of sulfur.

* * * * *